United States Patent [19]

Lees et al.

[11] Patent Number: 5,232,696

[45] Date of Patent: Aug. 3, 1993

[54] REDUCTION OF LOW DENSITY LIPOPROTEINS IN BIOLOGICAL FLUIDS

[75] Inventors: Robert S. Lees, Brookline; Robert S. Langer, Jr., Somerville; Claudy J. P. Mullon, Burlington; Hugh D. Conlon, Medford, all of Mass.

[73] Assignee: Massachusetts Institute of Technology, Cambridge, Mass.

[21] Appl. No.: 101,262

[22] Filed: Sep. 25, 1987

[51] Int. Cl.$^5$ .................. A61K 37/54; C12N 11/10; C12N 11/02; A61M 1/38
[52] U.S. Cl. ........................... 424/94.6; 604/5; 604/6; 435/2; 435/174; 435/177; 435/178; 435/197; 435/198
[58] Field of Search .............. 424/94.6, 101, 98; 435/2, 174, 177, 178, 197, 198; 604/5, 6

[56] References Cited

U.S. PATENT DOCUMENTS

4,775,483 10/1988 Mookerjea et al. .............. 210/670

OTHER PUBLICATIONS

Marmer et al, cited in Chem. Abstracts vol. 90:99580q (1979).
S. Parthasarathy et al., *Proc. Natl. Acad. Sci. USA*, 82:3000–3004 (1985).
P. Steinbrecher et al., *Proc. Natl. Acad. Sci. USA*, 81:3883–3887 (1984).
H. M. Verheij et al., *Biochimica et Biophysica Acta* 747:93–99 (1983).
Bergmeyer, H. U., *Methods of Enzymatic Analysis*, 3rd, 1983, Weinhein, Deerfield Beach, Florida, Verlag Chemie, pp. 283–284.
F. J. G. M. van Kuijak et al., *Trends in Biochemical Science*, 12(1), 31–34 (1987).
R. Langer, *Science*, 217:261–263 (1982).
M. S. Brown and J. L. Goldstein, *Science*, 232:34–47 (1986).
Christie, "Lipid Analysis", (Pergamon Press, N.Y., 1976), pp. 261–281.
Aggerbeck, L. P. et al., *J. Biol. Chem.*, 251:3823–3830 (1976).
Kleinman, Y. et al., *Arteriosclerosis*, 7:546a (1987).
Borensztajn, J. et al., *Arteriosclerosis*, 7:498a (1987).
Borensztajn, J. and T. J. Koltar, *Biochem. J.*, 200:547–553 (1981).

*Primary Examiner*—Jacqueline Stone
*Attorney, Agent, or Firm*—Cesari and McKenna

[57] ABSTRACT

A method and apparatus for reducing the levels of low density lipoproteins (LDL) in blood is disclosed. The LDL is contacted with an enzyme which modifies it in a manner such that the LDL is rapidly removed endogenously by the patients' own metabolic processes. The enzyme may be introduced into the patient by injection, transdermal transport, nasal insufflation and ingestion. Additionally, the enzyme may be contained in a reactor for both in vivo and extracorporeal use.

6 Claims, 2 Drawing Sheets

REDUCTION OF LOW DENSITY LIPOPROTEINS IN BIOLOGICAL FLUIDS

BACKGROUND OF THE INVENTION

Coronary heart disease (CHD) accounts for more deaths annually than any other disease, including all forms of cancer combined. Observational epidemiologic studies have established that the higher the total plasma cholesterol and low density lipoprotein cholesterol (LDL-C) levels, the greater the risk that CHD will develop.

LDL is spherical with a mass of approximately $2.5-3.0 \times 10^6$ Daltons and a diameter of approximately 21-23 nanometers. Each LDL particle contains approximately 1500 molecules of cholesteryl ester in an oily core that is shielded from aqueous plasma by a hydrophilic coat composed of approximately 800 molecules of phospholipids, 500 molecules of unesterified cholesterol, and a 510,000-dalton protein called apoprotein B-100 or Apo B.

Total plasma cholesterol and LDL-C levels may be reduced by diets, drugs and selective removal of low density lipoproteins from the blood. However, most drugs have potentially severe side effects. More specifically, drugs that decrease cholesterol synthesis may cause serious liver injury, cataracts and fetal abnormalities. Moreover, in familial hypercholesterolemia, homozygous individuals and many heterozygotes are resistant to drug therapy.

The direct removal of a patients' blood plasma with high LDL content, removal of LDL by plasmapheresis and replacement with a low-LDL or LDL-free fluid has been shown to be effective in lowering the plasma concentration of cholesterol and low density lipoproteins. However, although plasmapheresis is a largely successful therapy, it is a nonspecific technique which is extremely expensive, primarily because the replacement fluid must be a plasma fraction.

Two affinity-column adsorption methods, one using a polyanion (heparin/agarose or dextran sulfate) and the other using anti-LDL antibodies bound to agarose, have been evaluated experimentally to selectively remove LDL. With these systems, plasma replacement is unnecessary but a pair of columns containing the affinity ligand is generally used to obviate the limited capacity of these systems, rendering these techniques difficult and expensive to make and to operate.

SUMMARY OF THE INVENTION

This invention pertains to the use of an enzyme to modify LDL in a manner such that it is rapidly removed endogenously by a patients' own metabolic processes with the cholesterol contained therein excreted via the stools. One embodiment of the invention is a method of lowering LDL levels in blood using a process which comprises:

a) immobilizing an enzyme capable of hydrolyzing an ester bond at position 2 of glycerophospholipids present in LDL;

b) contacting the LDL-containing blood or plasma with the enzyme to hydrolyze an ester bond at position 2 of glycerophospolipids present in LDL, thus modifying the LDL in a manner which allows the modified LDL to be metabolized; and c) circulating the blood or plasma thus treated in the subject's blood stream for ultimate metabolism of the modified LDL.

Another embodiment comprises a reactor in which the enzyme is contained, the reactor designed to allow unmodified-LDL-containing blood to enter, become modified, and, exit the reactor.

Removal of low density lipoproteins from blood using enzymatic methods offers inherent advantages compared to methods heretofore described in the art. For example, enzymes are catalysts which offer the advantage of binding, modifying and releasing the substrate, so an apparatus using enzymes to modify LDL lends itself to a long-term useful life requiring little or no maintenance.

DETAILED DESCRIPTION OF THE INVENTION

Figure 1:
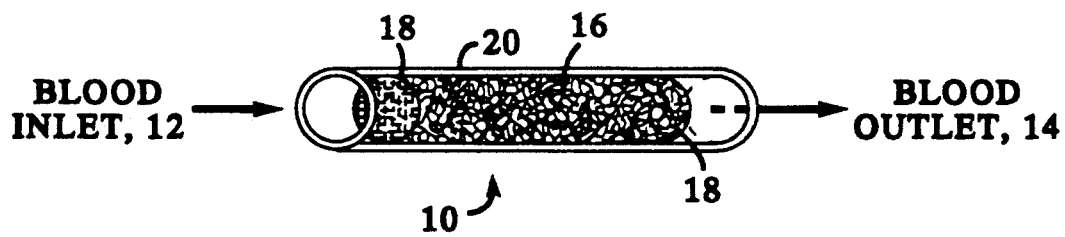
FIG. 1 is a schematic representation of an implantable enzyme reactor suitable for in-vivo modification of LDL contained in blood.

Reduction of low density lipoproteins can be achieved enzymatically. Specifically, an enzyme can be used to catalyze a reaction between water and glycerophospholipid to yield a lysoglycerophospholipid and a fatty acid. This occurs by the hydrolysis of the acyl residues specifically at the 2-position of the glycerol skeleton. The resulting modified LDL is then removed endogenously by the patient's metabolic process, and its cholesterol excreted via the stools.

Among the enzymes known to modify LDL in the desired manner are phospholipase $A_2$. Phospholipase $A_2$ can be obtained from a number of sources including bee venom, snake venom and porcine pancreas. Each of these is available commercially from companies such as Sigma Chemical Co., St. Louis Mo. Ideally, human phospholipase $A_2$ is preferred as it is the most compatible with the human immune system. At present, only small quantities of human phospholipase $A_2$ are available, however, as enzyme production techniques improve, the supply is expected to increase.

A number of methods for contacting LDL-containing blood with the modifying enzyme can be employed. In the preferred embodiment, however, the enzyme is immobilized or entrapped on or within an enzyme carrier such as agarose beads, membranes or hollow fibers. The enzyme carrier can be contained in a reactor suitable for extracorporeal, or ideally internal use. The internal version can be either implanted or inserted into a body cavity. In addition, immobilized enzyme reactors can also be used to provide extracorporeal modification of LDL-containing blood.

Preferred enzyme dosages can vary widely depending upon factors such as the level of LDL modification desired, and the time period of enzyme contact desired. Another consideration involves the level of LDL.

For example, in a patient in which the LDL level should be reduced by about 50%, a lower enzyme dose is required than for a patient in which the LDL level should be reduced by 75%. Thus, depending upon patient size, level of LDL modification desired, and various other considerations the enzyme dosage is expected to vary between about 10 to about 200 mg for a human adult with even greater dosage ranges conceivable. As there are approximately 800 enzyme units per milligram of protein, this corresponds to a dose of between about 8,000 to about 160,000 enzyme units.

Another consideration in enzyme effectiveness is the presence of enzyme cofactors. As used herein, an enzyme cofactor is defined as an accessory substance that is not an enzyme, but is necessary for proper enzyme function. For example, phospholipase $A_2$ is known to demonstrate enhanced activity in the presence ions such as $Ca^{+2}$ and $Mg^{+2}$. While these ions are necessary for maximum enzyme performance, it is not necessary to add them to the enzyme prior to contacting the enzyme with a patient's blood because they are almost always naturally present in blood in quantities great enough to enhance enzymatic activity to its highest level.

A schematic representation of one embodiment of an implantable enzyme reactor is shown in FIG. 1. The reactor, generally represented 10, comprises a tube 20, containing a blood inlet 12 and a blood outlet 14. Contained within the tube is an enzyme, preferably phospholipase $A_2$ enzyme immobilized onto an insoluble support such as agarose beads 16. Baffles or screens 18 positioned at either end of the enzyme-containing bead bed are used to retain the beads within the reaction tube. In operation, blood containing LDL enters the reactor 10 at blood inlet 12. The blood passes through the first baffle 18, and into the immobilized enzyme bed 16. The enzyme immobilized on the bed modifies the LDL contained within the blood, thereby allowing it to be metabolized by the patient's natural metabolic processes. The blood containing the now modified LDL passes through a second baffle 18 and exits the reactor at blood outlet 14. The blood continues to pass through the patient until it reaches the patient's liver where the modified LDL is metabolized.

Figure 2:
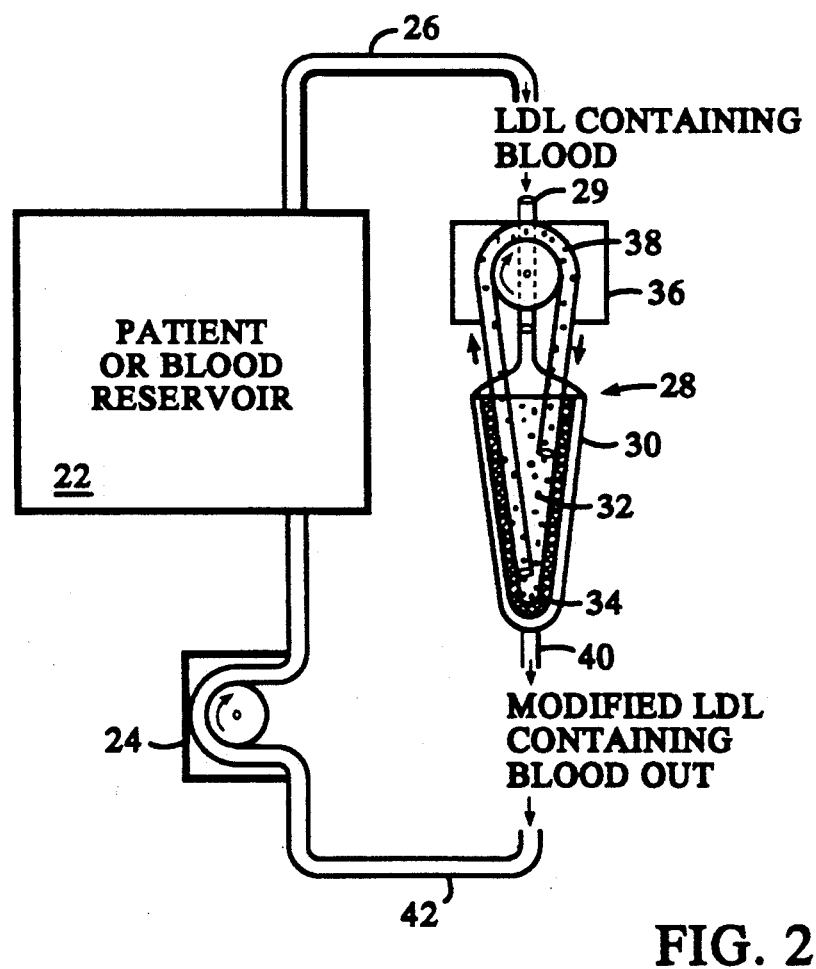
FIG. 2 is a schematic representation of an enzyme reactor suitable for extracorporeal modification of LDL contained in blood.

FIG. 2 is a schematic representation of one embodiment of an extracorporeal reaction system for modifying LDL in blood. Blood to be processed is removed from a patient 22 via a peristaltic pump 24, into an inlet tube 26. From the inlet tube, the blood enters the extracorporeal reactor, generally represented 28, at inlet 29. The extracorporeal reactor comprises a shell 30, a suspension of beads containing an immoblized enzyme 32, a filter 34, a peristaltic pump 36, a recirculation tube 38 and a blood outlet 40.

Once blood enters the reactor 28 at inlet 29, it contacts the enzymatic suspension 32. The enzymes modify LDL contained within the blood, thereby allowing it to be metabolized by the patient's natural metabolic processes. The blood/suspension mixture is circulated by a peristaltic pump 36 and a recirculation tube 38 to provide good LDL/enzyme contact. The filter 34 serves to keep the enzyme containing beads of the suspension 32 within the reactor shell 30. The processed blood exits the reactor 28 at blood outlet 40 and travels through a return tube 42 back into the patient 22, thereby completing the process circuit.

Further details of the invention may be obtained in the following examples.

EXAMPLE 1: PHOSPHOLIPASE $A_2$ MODIFICATION OF LDL AND RABBIT STUDIES OF ITS REMOVAL

Agarose beads containing 4,000 to 10,000 units of immobilized phospholipase $A_2$ per gram of agarose were deposited into a sinter glass funnel. They were washed with distilled water and a phosphate buffered saline (PBS) buffer. The beads were dried by drawing air through them and then placed in the reaction vessel. The reaction vessel was then filled with a mixture of PBS buffer (pH=7.6), 5 mM $Ca^{+2}$, 1% bovine serum albumen (BSA) and 2 mg low density lipoprotein (LDL). Once filled, the reaction vessel was sealed leaving only a small air pocket. The reaction vessel was shaken for 3 hours at 37° C. The density of the reaction solution was adjusted to $1.063\rho$ using a NaBr-NaCl solution with a density of $1.287\rho$. This solution was then spun in an ultracentrifuge at 40,000 rpm for 22 hours.

The top layer of the centrifuged solution, (which has an orange color) was removed and placed into a dialysis bag. This was then dialyzed for 18 hours against 1 liter of a 1.006 saline solution at 4° C.

1 mg of the dialyzed phospholipase $A_2$-modified-LDL ($PA_2$-LDL) was iodinated using 1 mCi Na $^{125}$I using the ICl method. The resulting $^{125}$I-$PA_2$-LDL solution was then dialyzed for 24 hours against 1 liter of 1.006 saline maintained at 4° C.

Immediately after the dialysis was completed, the $^{125}$I-$PA_2$-LDL solution was tested for precipitability. If the precipitability was found to be greater then 95%, 200μCi of the solution was injected into a vein located in a rabbits ear. 1 ml blood samples were drawn from an artery located in a rabbits ear at different time intervals. This withdrawn blood was then spun to separate the plasma and 100 μl of plasma was counted in a gamma counter.

The number of counts at each time point was divided by the total counts injected and then multiplied by 100 to calculate the percent counts remaining in the plasma. This data was then plotted against time to give a die-away curve.

Figure 3:
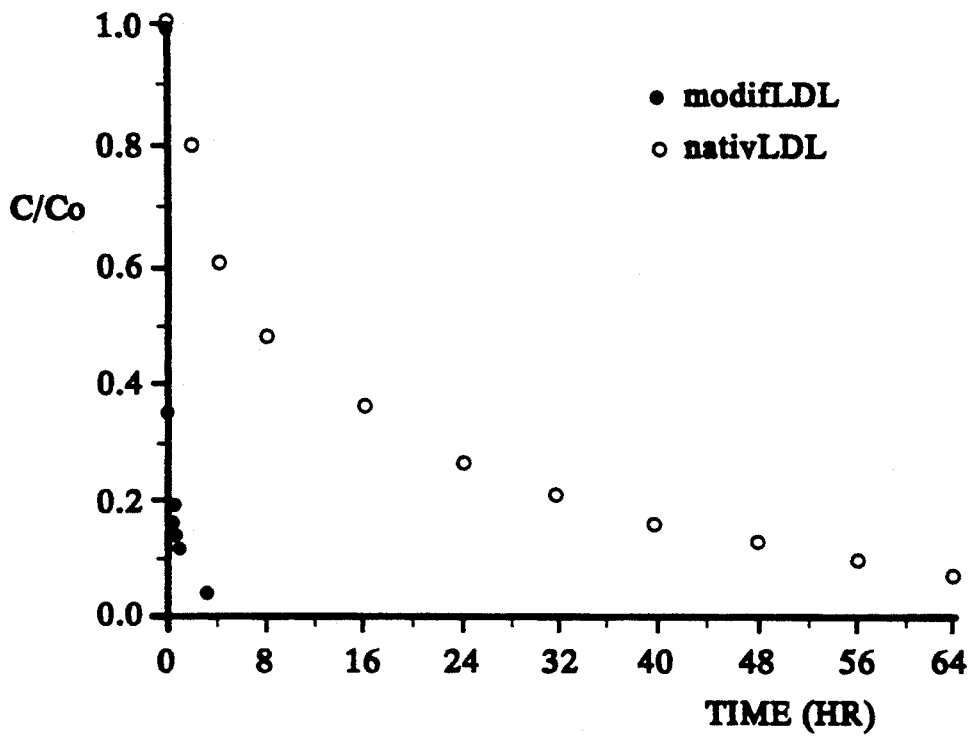
FIG. 3 represents the die-away curve of phospholipase $A_2$-modified human LDL in rabbits over a 64 hour period.

FIG. 3 is a die away curve of phospholipase $A_2$ modified human LDL in rabbits as determined in the above procedure. In FIG. 3, the relative plasma concentration of LDL (defined as instantaneous concentration, C, over initial concentration, $C_o$) is plotted as a function of time over a 64 hour period.

Figure 4:
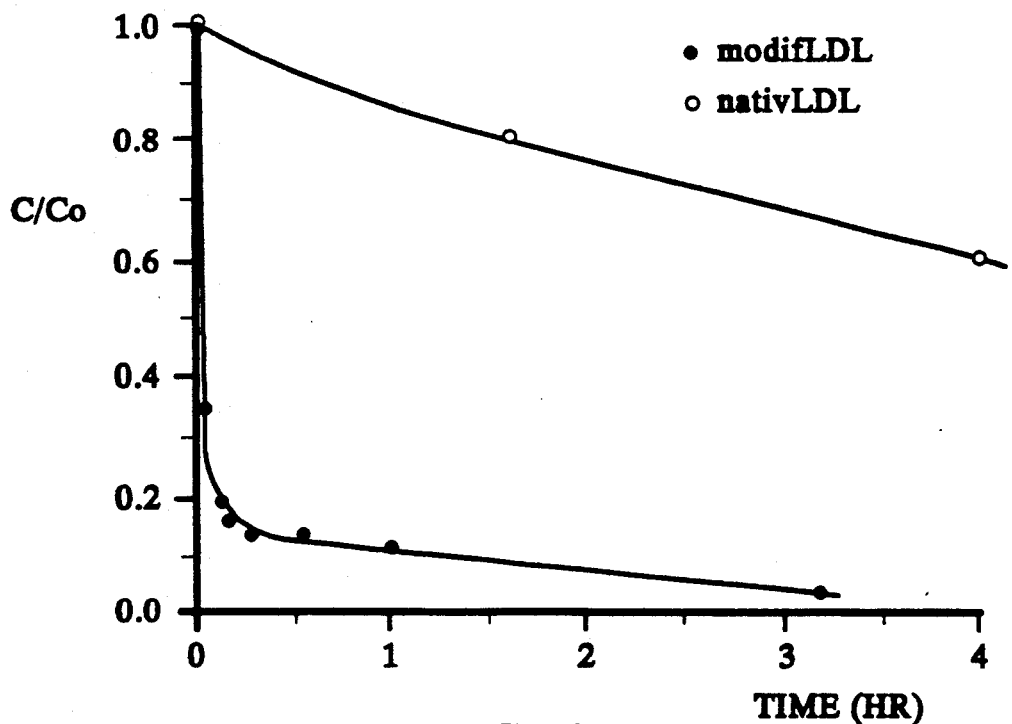
FIG. 4 represents the die-away curve of phospholipase $A_2$-modified human LDL in rabbits over a 4 hour period.

FIG. 4 is based upon the same data as FIG. 3, except that it only shows the first 4 hours of the experiment in order to more conveniently demonstrate the die-away characteristics of the modified LDL.

In both figures, it is readily observed that the enzyme-modified human LDL is eliminated from the rabbit at a faster rate than that of native human LDL.

Interestingly, the die away curve of the is a steep, almost vertical domain which lasts for about 15 minutes after enzyme-modified LDL injection. The second domain is much shallower and approximates that of LDL die off for LDL which has not been enzymatically modified. This shallower die off curve is likely that of LDL, which although in the presence of the modifying enzyme, has not been modified by the enzyme and thus dies off at the same rate as native LDL. Comparison of the two domains and also the region in which the second begins to dominate is important as it can be used to provide data useful for determining the ideal enzyme dosage for a given set of starting conditions.

EXAMPLE 2: ANALYSIS OF PHOSPHOLIPASE A$_2$ MODIFIED LDL

Human plasma and native LDL treated with soluble and immobilized phospholipase A$_2$ have been analyzed for free fatty acid content using thin layer and gas liquid chromotography techniques. Unsaturated free fatty acids, essentially linoleic acid, increased in concentration in both enzymatically treated plasma and isolated native LDL. Paper electrophoresis of modified LDL and human plasma showed a faster migration of the modified LDL band compared with native LDL and plasma controls. This result suggests that LDL is modified by phospholipase A$_2$ in such a way that its net negative charge is increased. Size exclusion HPLC analysis of modified LDL showed a single peak comparable to native LDL. This suggests the absence of LDL aggregate formation after enzymatic modification and is consistent with the observed increase in the particle net charge, thereby making it less likely to aggregate.

EQUIVALENTS

Those skilled in the art will recognize, or be able to ascertain employing no more than routine experimentation, many equivalents to the specific materials, steps, etc., described above. Such equivalents are intended to be covered by the following claims.

We claim:

1. A method for lowering the level of low density lipoprotein (LDL) in a subject's blood, which method comprises the steps of:
   a) immobilizing on a surface an enzyme selected from the group consisting of phospholipases A$_s$;
   b) contacting the LDL-containing whole blood or plasma with the immobilized enzyme to hydrolyze an ester bond at position 2 of glycerophospholipids present in LDL, thus modifying the LFL in a manner which allows the modified LDL to be more rapidly metabolized; and,
   c) circulating the modified LDL-containing whole blood or plasma in the subject's blood stream for ultimate metabolism of the modified LDL.

2. The method of claim 1 wherein the phospholipase A$_2$ is selected from the group consisting of bee venom phospholipase A$_2$, snake venom enzyme, and porcine phospholipase A$_2$ and human phospholipase A$_2$.

3. The method of claim 1 wherein the enzyme is allowed to contact the subject's blood extracorporeally.

4. The method of claim 1 wherein the enzyme is allowed to contact the subject's blood components intracorporeally.

5. The method of claim 4 wherein the enzyme enters the subject's body by implantation.

6. The method of claim 1 wherein the enzyme is immobilized on a surface selected from the group consisting of agarose beads, membranes and hollow fibers.

* * * * *